(12) United States Patent
Giorno (10) Patent No.: US 7,033,174 B2
(45) Date of Patent: Apr. 25, 2006

(54) PROSTHETIC MOUNTING DEVICE

(76) Inventor: Thierry Giorno, 18 Avenue Sevigne, Nice (FR) 06100

( * ) Notice: Subject to any disclaimer, the term of this patent is extended or adjusted under 35 U.S.C. 154(b) by 0 days.

(21) Appl. No.: 10/165,332

(22) Filed: Jun. 7, 2002

(65) Prior Publication Data

US 2003/0228556 A1 Dec. 11, 2003

(51) Int. Cl.
*A61C 8/00* (2006.01)
(52) U.S. Cl. ...................................................... 433/174
(58) Field of Classification Search ................ 433/173, 433/174, 225
See application file for complete search history.

(56) References Cited

U.S. PATENT DOCUMENTS

| | | | |
|---|---|---|---|
| 3,466,748 A * | 9/1969 | Christensen | 433/189 |
| 4,193,194 A | 3/1980 | Dalise | |
| 4,202,101 A * | 5/1980 | Weissman | 433/225 |
| 4,728,292 A * | 3/1988 | Lustig et al. | 433/225 |
| 4,767,332 A * | 8/1988 | Weissman | 433/225 |
| 4,826,434 A * | 5/1989 | Krueger | 433/174 |
| 5,205,745 A * | 4/1993 | Kamiya et al. | 433/173 |
| 5,263,996 A * | 11/1993 | Fihol | 433/221 |
| 5,312,255 A * | 5/1994 | Bauer | 433/174 |
| 5,639,237 A * | 6/1997 | Fontenot | 433/173 |
| 5,662,475 A * | 9/1997 | Mena | 433/172 |
| 5,749,732 A | 5/1998 | Sendax | |
| 5,967,783 A * | 10/1999 | Ura | 433/174 |
| 6,716,030 B1 * | 4/2004 | Bulard et al. | 433/174 |

OTHER PUBLICATIONS

WWW.jaeilcorp.co.kr/imtec3-1.htm web page advertisement for IMTEC Sendax Mini Dental Implants, copyright 2001.*
IMTEC Sendax Mini Dental Implant System (MDI) Small Wonder 4-page color brochure, no date.
Dental Attachment Systems The AIT Attachment for Retained Natural Tooth Roots pp. 6 and 7, no date.

* cited by examiner

*Primary Examiner*—Ralph A. Lewis
(74) *Attorney, Agent, or Firm*—Reising, Ethington, Barnes, Kisselle, P.C.

(57) ABSTRACT

A prosthetic mounting device for securing a prosthetic device on bone tissue. The device includes a bone screw and a prosthetic abutment attached to an aft end of the screw. The abutment engages and rigidly supports a prosthesis. A tapered collar extends radially outward from around the aft end of the threaded shaft. In one embodiment, the device also includes an installation handle connected to and extending axially from the abutment. A rotary driver is used to engage and rotate the handle. The handle detaches from the abutment under a predetermined torque load both to cue an installer that increased bone density requires that a different instrument be used and that bone density is sufficient to support both initial and long-term stabilization.

13 Claims, 6 Drawing Sheets

PROSTHETIC MOUNTING DEVICE

CROSS-REFERENCES TO RELATED APPLICATIONS

Not Applicable

STATEMENT REGARDING FEDERALLY SPONSORED RESEARCH OR DEVELOPMENT

Not Applicable

BACKGROUND OF THE INVENTION

FIELD OF THE INVENTION

This invention relates generally to a prosthetic mounting device for securing a prosthetic device on bone tissue.

DESCRIPTION OF THE RELATED ART INCLUDING INFORMATION DISCLOSED UNDER 37 CFR 1.97 AND 1.98

Conventional crowns, bridges and dentures have long been the standard prosthetic devices used to replace missing teeth. Such devices are secured to a jaw bone using a surgical anchor known as a dental implant or a prosthetic mounting device.

The design of dental implants has developed considerably over the years since their initial conception by the ancient Egyptians. One of the more important developments is credited to the Swedish firm, Noblepharma. In the mid-1980s, Noblepharma developed and marketed a dental implant that resembled a natural tooth root. This implant, known as a root form implant, include two major components: a bone screw and a prosthetic abutment interface. There are now about 10 major dental implant manufacturers in the United States alone that market various forms of the root form implant.

The protocol for surgical placement of a root form implant is to first expose an underlying jaw bone through a surgical intervention of the soft tissue covering the jaw bone. An opening is then created in the jaw bone equal to the minor diameter of the bone screw portion of the implant. This is done by using a series of expanding diameter surgical drills that allow the surgeon to gradually increase the size of the hole in the bone until the implant can be screwed into place. Once the implant has been screwed in, the soft tissue incision is sutured closed over the osteotomy site. In a process known in the art as osseointegration, the bone tissue around the device then grows into tight apposition to the screw during a three to six month healing process.

In recent years, however, some doctors have advocated what is known in the art as immediate or progressive loading of an implant. This process eliminates or shortens the time required for osseointegration and its associated long healing times. However, most implants still require that patients wait for an extended time before they can fully make use of permanent replacement teeth. Multiple surgeries are also required.

After a root form screw implant is firmly positioned in bone, and once the osseointegration process is complete, the tissue covering the osteotomy site is again reflected and an attachment device called an abutment is affixed to a head of the implant that remains exposed after installation. A dental prosthetic can then be cemented or screwed onto the prosthetic abutment portion of the implant. The prosthetic abutment portion of the device is available in many shapes, sizes and designs to accommodate various treatment applications.

Extending healing periods and costs associated with the above described two-stage surgical implant procedure have prevented traditional dental implant systems from becoming the chosen treatment modality for patients with missing teeth. Manufacturers and marketers of dental implants have been searching for new concepts and ideas that would provide a more economical and less surgically invasive system.

In response to this need, a New York City general dentist by the name of Dr. Victor I. Sendax began experimenting with endodontic posts designed to be implanted directly into a jaw bone. The Sendax implants had a one-piece design incorporating both screw and abutment. Because the diameter of Dr. Sendax's implant was only 1.8 mm, Dr. Sendax was able to develop an implantation procedure that did not require a large opening in the bone to receive the implant. All that was necessary was a small, shallow starter hole that could be formed in jaw bone tissue directly through soft tissue without having to surgically lay back a flap of the soft tissue to expose the bone beneath. This new approach was minimally invasive and provided an implant that could be immediately loaded without having to wait for an extended period of time for osseointegration to occur. In the art, this new type of implant that's dimensionally small enough to self-tap into bone tissue without splitting the bone tissue, became known as the mini dental implant.

While some standard sized (approx. 3.75 mm diameter) implants claim to be self-tapping, because of their larger size, the extent of their self-tapping is severely limited. Bone has a visco-elastic nature that allows it stretch, to a certain point, to accommodate inserted objects. However, to install an implant shaft larger than approximately 2.0 mm in diameter requires a large osteotomy formed by drilling progressively larger osteotomy holes to the full depth that the implant will extend into the bone. For example, a so-called self-tapping implant having a 3.75 mm diameter and 4.0 mm diameter threads will still require a 3.75 mm osteotomy. A cutter is supported near the tip of such an implant and extends radially outward to engage and form thread grooves in the wall of a 3.75 mm osteotomy as the implant is installed.

IMTEC® Corporation is currently marketing a Sendax mini dental implant system that comprises a prosthetic mounting device having a threaded shaft, and an abutment including a square nut and a ball-shaped O-ring abutment. The threaded shaft is tapered at a first end to allow the shaft to self-tap into bone tissue starting from a small, shallow pilot hole formed in bone tissue. Because the shaft self-taps past the depth of the pilot hole, it immediately integrates with the bone tissue. The square nut is attached to and extends integrally and axially from a second end of the threaded shaft opposite the first end. The O-ring abutment is attached to and extends integrally and axially from the square abutment. The O-ring abutment is shaped to engage and rigidly support a prosthetic tooth or set of teeth. However, this system is unable to disconnect or automatically discontinue torque application during installation when a predetermined bone density is encountered. Nor can such a device warn an installer that the bone tissue lacks sufficient density to properly support a prosthetic tooth. Still further, the Sendax mounting system cannot indicate to an installer when it is fully seated in bone tissue, the platform formed at the head area of the shaft is no greater than the cross-sectional area of the shaft itself and provides little support for a prosthesis, and it doesn't provide a satisfactory interface between the implant and surrounding soft tissues.

What is needed, therefore, is a prosthetic mounting device that can give an installer an indication of when the implant is fully seated, can provide greater support and stability to a prosthesis mounted on it, and provides a beneficial interface between the device and surrounding soft tissues. What is also needed is such a device that can disconnect torque application during installation when a predetermined bone density is encountered can indicate to an installer that the supporting bone tissue is of insufficient density.

BRIEF SUMMARY OF THE INVENTION

The invention is a prosthetic mounting device for securing a prosthetic device on bone tissue. The device comprises a threaded shaft configured to be screwed into bone tissue and a prosthetic abutment attached to and axially extending from an aft end of the shaft. The abutment is configured to engage and rigidly support a prosthesis. The prosthetic mounting device also includes a collar extending radially outward from around the aft end of the threaded shaft and tapered to accommodate surrounding gingival tissue by emulating the tapered configuration of a natural tooth.

The invention also includes a method for securing on bone tissue a prosthetic device comprising a prosthetic abutment attached to and axially extending from an aft end of a threaded shaft, the abutment including an O-ball and a nut disposed between the O-ball and the threaded shaft. The method includes providing a driver adapter comprising an recess configured to receive the O-ball and nut, to releasably retain the O-ball, and to drivingly and releasably engage the nut. The driver adapter is connected to the mounting device such that an inner chamber of the recess engages and axially retains the O-ball and an outer portion of the recess rotatably engages the nut. A rotary driver is then connected to the driver adapter and the mounting device is screwed into bone tissue by engaging the threaded shaft with the bone tissue and operating the rotary driver to rotate the driver adapter and mounting device.

According to another aspect of the invention, the prosthetic mounting device also includes an installation handle connected to and extending axially from the abutment. The handle is configured to be engaged and rotated by a rotary driver and to detach from the abutment under a predetermined torque load so that the handle breaks off when bone of a predetermined density is encountered. This prevents an installer from continuing to use the rotary driver when bone density requires that a different instrument, such as a ratchet wrench, be used for the remainder of the installation. It also indicates to an installer that bone density is sufficient to support both initial and long-term stabilization. If the handle never breaks off during installation, the installer knows that bone tissue density is insufficient to properly support a prosthesis. The invention also includes a method for securing on bone tissue a prosthetic device comprising a prosthetic abutment attached to and axially extending from an aft end of a threaded shaft and an installation handle removably attached to and extending axially from the abutment, the handle being configured to detach under application of a predetermined torque load. A rotary driver is connected to the installation handle and the mounting device is screwed into bone tissue by engaging the threaded shaft with the bone tissue and operating the rotary driver to rotate the device until the handle breaks off.

The invention also includes a method for determining whether bone tissue is sufficiently dense to properly support a prosthetic mounting device. According to this method a prosthetic mounting device is provided that comprises a prosthetic abutment attached to and axially extending from an aft end of a threaded shaft and an installation handle removably attached to and extending axially from the abutment, the handle being configured to detach under application of a predetermined torque load experienced when the device encounters bone tissue of sufficient density to properly support a prosthetic mounting device. The mounting device is screwed into bone tissue by engaging the threaded shaft with the bone tissue and operating the rotary driver to rotate the device until either the handle breaks off or the threaded shaft is seated to a predetermined depth in the bone tissue. The handle, by remaining attached to the abutment until the threaded shaft reaches the predetermined depth, indicates to an installer that the bone tissue at that site is insufficiently dense to properly support a prosthesis.

Also according to the invention a prosthetic mounting system is provided for securing a prosthetic device on bone tissue. The system comprises a prosthetic mounting device and a driver adapter. The prosthetic mounting device includes a prosthetic abutment attached to and axially extending from an aft end of a threaded shaft, the abutment including a nut. The driver adapter has a recess configured to receive and to releasably and drivingly engage the nut. The driver adapter recess is defined by a socket having a leading rim positioned to contact an upper surface of a gingival tissue layer when the threaded shaft portion of the prosthetic mounting device has been driven to a proper depth into bone tissue beneath the gingival tissue layer.

According to another aspect of the inventive system, the leading rim of the driver adapter socket is positioned to contact an upper surface of a gingival tissue layer when the threaded shaft portion of the prosthetic mounting device has been driven to a depth into bone that leaves protruding from an upper surface of the bone an upper portion of the collar. In this positino, the protruding upper portion of the collar laterally abuts a surrounding portion of a gingival tissue layer overlying the bone.

The invention also includes a method for securing a prosthetic device on bone tissue. According to this method, a prosthetic mounting device is provided that comprises a prosthetic abutment attached to and axially extending from an aft end of a threaded shaft, the abutment including a nut disposed adjacent the threaded shaft. A driver adapter is provided that comprises a recess configured to drivingly and releasably engage the nut at a depth within the recess that places the mounting device at a desired depth when a leading rim of the driver adapter contacts gingival tissue. The driver adapter is connected to the mounting device such that an axially outer portion of the recess rotatably engages the nut and a rotary driver is connected to the driver adapter. The mounting device is then screwed into bone tissue by engaging the threaded shaft in the bone tissue and operating the rotary driver to rotate the driver adapter and mounting device. Proper mounting device depth is determined as being the depth of the mounting device when the leading rim of the driver adapter socket contacts gingival tissue.

BRIEF DESCRIPTION OF THE SEVERAL VIEWS OF THE DRAWINGS

These and other features and advantages of the invention will become apparent to those skilled in the art in connection with the following detailed description and drawings, in which.

DETAILED DESCRIPTION OF INVENTION EMBODIMENT(S)

A first embodiment of a prosthetic mounting device for securing a prosthesis such as a prosthetic tooth on bone tissue 14 is generally shown at 10 in FIGS. 1–7. A second embodiment is shown at 10' in FIGS. 9 and 10. Reference numerals with the designation prime (') in FIGS. 9 and 10, and in FIGS. 8 and 11–14, indicate alternative configurations of elements that also appear in the first embodiment. Unless indicated otherwise, where a portion of the following description uses a reference numeral to refer to the figures, that portion of the description is intended to apply equally to elements designated by primed numerals in FIGS. 8–14.

Figures 1, 2, 3:
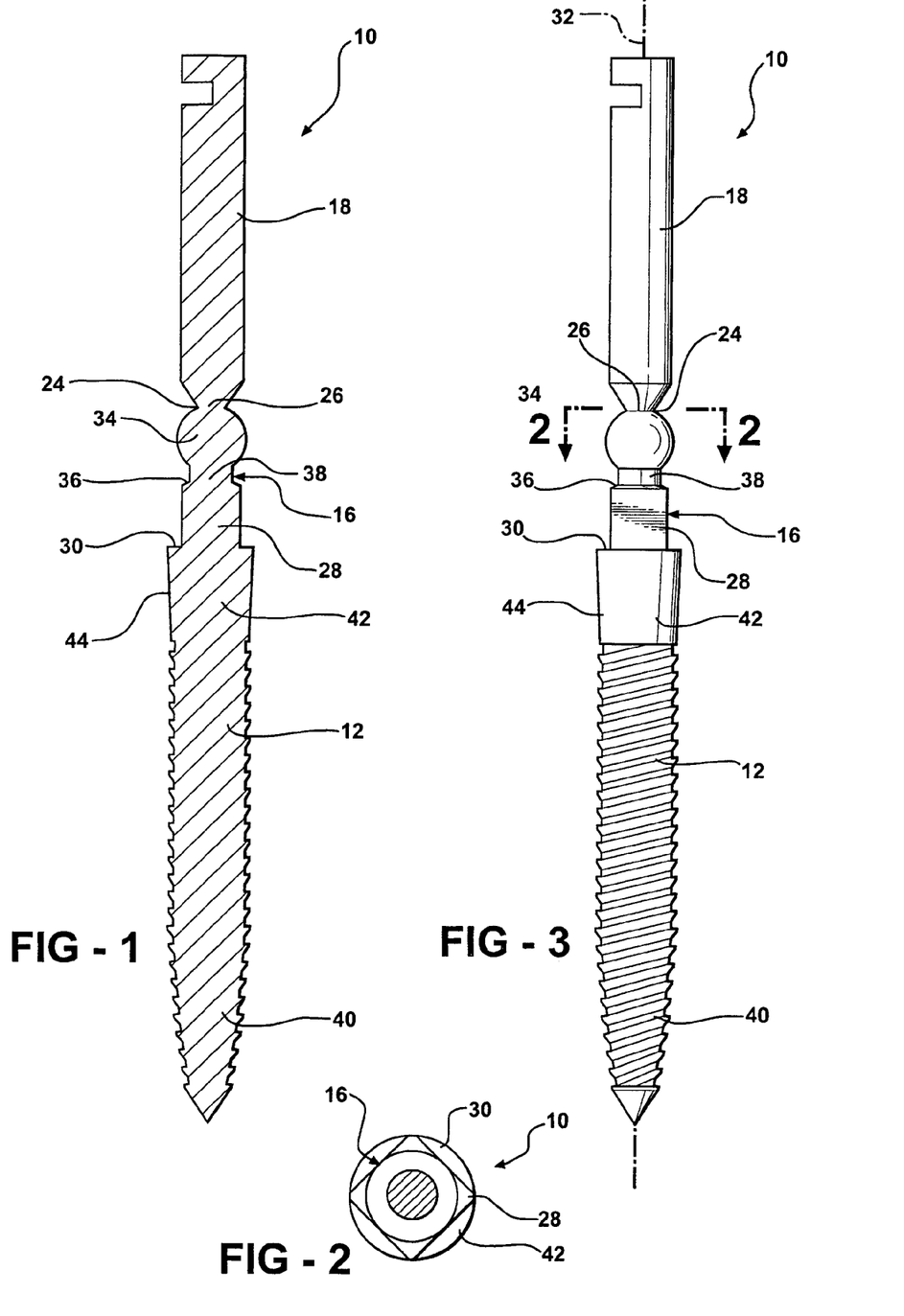
FIG. 1 is a front view of a prosthetic mounting device constructed according to a first embodiment of the invention.
FIG. 2 is a cross-sectional front view of the device of FIG. 1.
FIG. 3 is a cross-sectional view of the device of FIG. 1 taken along line 2—2 in FIG. 1.

The device 10 includes a threaded shaft 12 or bone screw that is screwed into bone tissue 14 and a prosthetic abutment 16 attached to and axially extending from an aft end of the shaft 12. The abutment 16 engages and rigidly supports a prosthesis to serve as an interface between the prosthetic mounting device 10 and a prosthesis. The device 10 also includes an installation handle 18 connected to and extending axially from the abutment 16. The handle 18 is engaged and rotated by a manual or motor driven rotary driver 20 and is detached from the abutment 16 under a pre-determined torque load so that the handle 18 breaks off when bone tissue of a pre-determined density is encountered. This prevents an installer from continuing to use the rotary driver 20 when bone density requires that a different instrument, such as a ratchet wrench 22, be used for the remainder of the installation. Detachment of the handle 18 also indicates to an installer that bone tissue density is sufficient to support both initial and long-term stabilization of a prosthesis. If the handle 18 never breaks off during installation, the installer knows that bone tissue 14 density is insufficient to properly support a prosthesis.

The handle 18 extends from an aft end 24 of the abutment 16 from a weakened area 26 that defines an interface between the handle 18 and the abutment 16. This weakened area 26 is configured to break under a pre-determined torque load of approximately 30 Newton-centimeters (30 Ncm). The handle 18, abutment 16, and shaft 12 are integrally formed with one another as a single unitary piece. The weak area is a neck formed at the interface between the handle 18 and the abutment 16.

The handle 18 is a contra-angle post that can be engaged and rotated by a low speed contra-angle rotary driver 20. The contra-angle rotary driver 20 rotates the device 10 at a speed in the range of approximately 20–50 rpm.

The abutment 16 includes a nut 28 fixed to and axially extending from an aft end 30 of the threaded shaft 12. The nut 28 is shaped to be engaged and rotated by a tool adapted for that purpose. As best shown in FIG. 2, the nut 28 has a square cross section as measured perpendicular to a rotational axis 32 of the device 10. The nut 28 can be engaged and rotated by a ratchet wrench 22 or similar implement having a complimentary shaped engagement structure. In other embodiments, a nut and complimentary wrench of any other suitable configuration may be used instead of a square nut 28 and a wrench 22 with a square nut engagement box.

The abutment 16 also includes an O-ring abutment 34 fixed to and axially extending from an aft end 36 of the nut 28. The O-ring abutment 34 is an annular, generally spherical appendage known in the art as an "O-ball." The O-ring abutment 34 is designed to engage an O-ring disposed within a prosthesis according to any one of a number of different methods known in the art. The O-ring abutment 34 has a neck portion 38 where the O-ring abutment 34 merges with the aft end of the nut 28.

The threaded shaft 12 includes a tapered portion 40 shaped to wedge the shaft 12 into bone tissue 14 and instantly integrate with the bone tissue 14 upon installation. This increases initial stabilization and makes it possible to affix a permanent prosthesis to the O-ring abutment 34 immediately following installation.

The device 10 includes a collar 42 extending radially outward from around the aft end of the threaded shaft 12. The collar 42 is shaped to arrest threaded insertion of the device 10 at its proper depth. The shape of the collar 42 includes a frusto-conical surface 44 tapering radially outward and back from the threaded portion 12 of the shaft 12 to a point adjacent the aft end 30 of the shaft 12. Unlike the shaft 12, which has a relatively rough surface for bone integration, the collar is polished to promote adjacent soft tissue growth. The device 10 comprises a titanium alloy.

Figure 4:
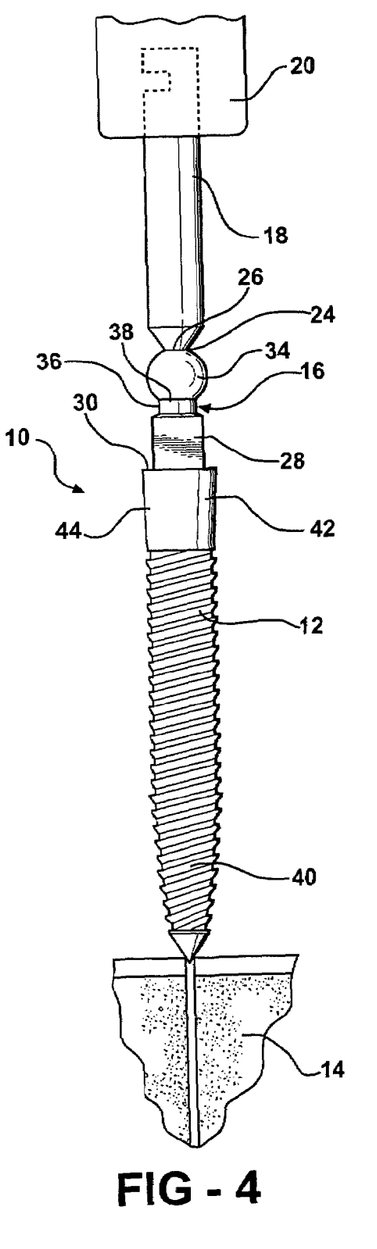
FIG. 4 is a front view of the prosthetic mounting device of FIG. 1 with a handle portion of the device connected to a rotary driver and a forward end of a threaded shaft portion of the device engaged in a small pilot hole formed in bone tissue.

In practice, a device 10 constructed according to the first embodiment of the invention can be secured in bone tissue 14 by first transporting the device 10 in a sterile condition within a sterile package. When the time comes to install the device 10, the package is opened and a rotary driver 20 is connected to the handle 18. The rotary driver 20 is then used to withdraw the device 10 from the package and to transport the device 10 to the surgical site. The mounting device 10 is then screwed into bone tissue 14 by first engaging the threaded shaft 12 with a pilot hole formed into the bone tissue 14 through the soft tissue 14 covering the jaw bone as shown in FIG. 4. The rotary driver 20 is then operated to rotate the device 10 until the handle 18 either breaks off or the device 10 is fully seated to a pre-determined depth.

Figure 5:
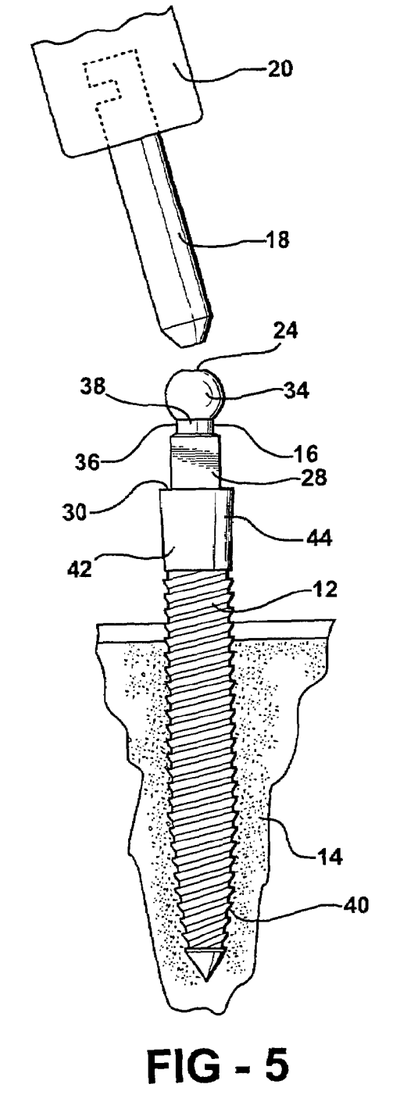
FIG. 5 is a front view of the prosthetic mounting device of FIG. 4 with the handle portion of the device broken off and the threaded shaft portion of the device partially screwed into the bone tissue.
Figure 6:
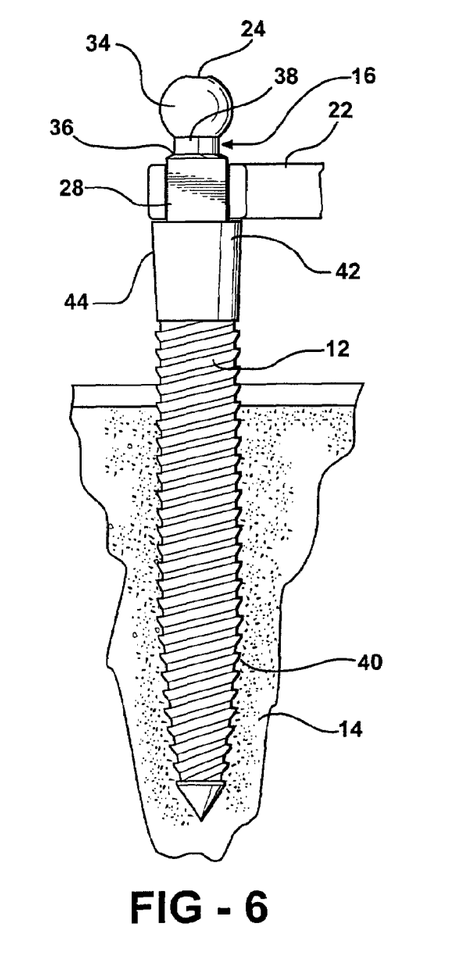
FIG. 6 is a front view of the prosthetic mounting device of FIGS. 4 and 5 with the handle portion removed and a ratchet wrench engaging a nut portion of an abutment of the device.
Figure 7:
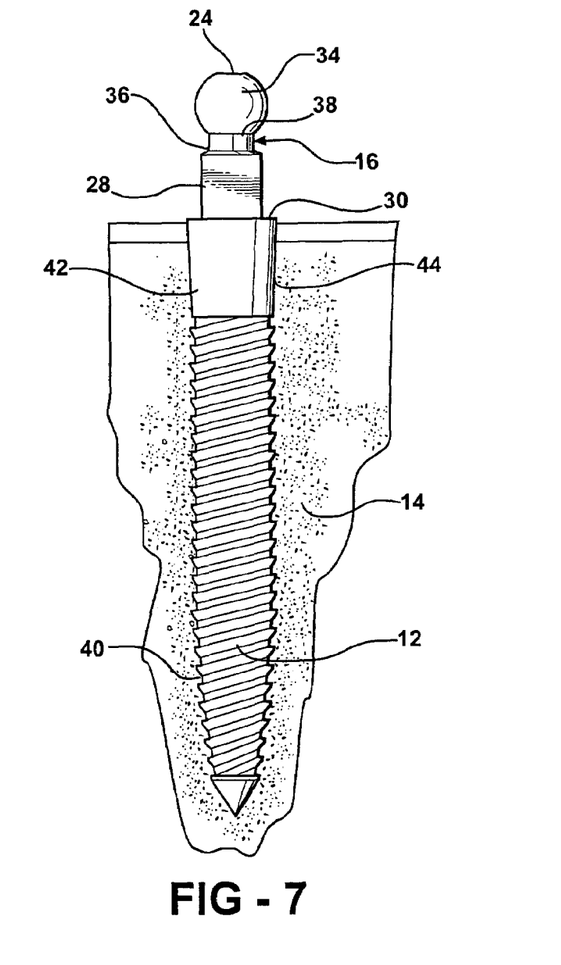
FIG. 7 is a front view of the prosthetic mounting device of FIGS. 4–6 shown after having been screwed into the bone tissue to a full desired depth.

If bone density is sufficient to properly support the device 10 and an attached prosthesis, the handle 18 breaks off before the device 10 reaches its full pre-determined depth as shown in FIG. 5. The mounting device 10 is then screwed to its full desired depth in the bone tissue 14 as shown in FIG. 7. This is accomplished by engaging and rotating the prosthetic abutment 16 with a manual ratchet wrench 22 or similar implement as shown in FIG. 6.

If the handle 18 does not break off before the device 10 reaches its desired depth, the mounting device 10 is removed from the bone tissue 14 and an alternative prosthetic mounting method and/or device 10 more adaptable to supporting a prosthesis on soft bone tissue 14 is selected.

In addition to its breakaway feature, the installation handle 18 of the device 10 provides a hands-free delivery system. It allows a device 10 to be retrieved from a sterile container and transported to a surgical site without contaminating the portion of the shaft 12 to be implanted in bone tissue 14. The handle 18 also serves to transmit torque from a rotary driver 20 to the device 10 for threading the device 10 into bone tissue 14 without damaging the abutment 16. Abutment 16 damage can comprise secure attachment of a prosthesis to the device 10.

The device 10 is a "mini" dental implant dimensioned to self-tap into bone tissue starting at a small, approximately ¼" deep starter hole. The shaft portion 12 of the device 10 is approx. 1.8 mm in diameter. However, in other embodiments, the shaft may be up to approximately 2 mm in diameter depending on the visco-elastic properties of the bone.

The second prosthetic mounting device embodiment 10' is essentially identical to the first embodiment 10 except that the second embodiment includes no installation handle. Instead, as shown in FIG. 8, an O-ball 34' defines an upper end of the device 10'.

Figure 13:
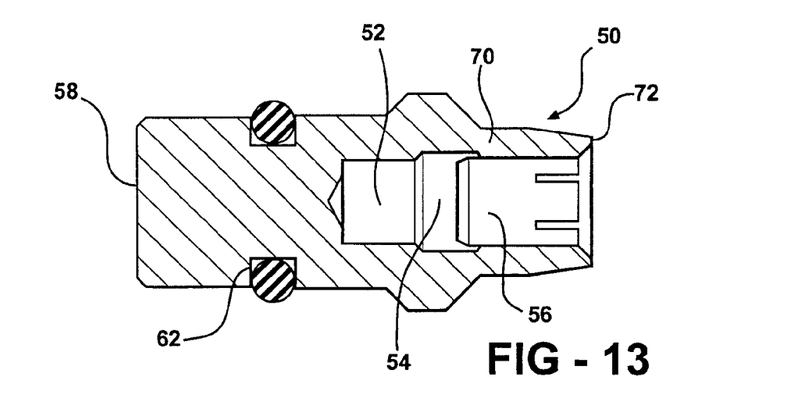
FIG. 13 is a cross-sectional front view of the driver adapter of FIG. 9.
Figure 14:
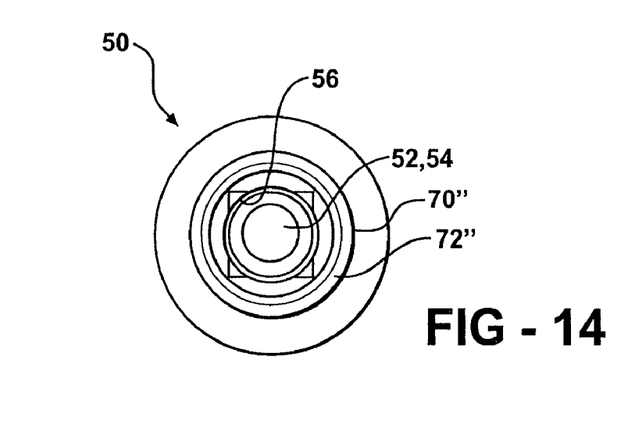
FIG. 14 is an end view of the driver adapter of FIG. 9 showing an end opposite the end shown in FIG. 12.

Because the second mounting device embodiment 10' includes no integral installation handle, the invention also comprises a driver adapter 50 that receives the O-ball 34' and the square nut 28' into a complementary-shaped recess that's best shown at 52 in FIG. 13. An inner chamber 54 of the recess 52 is shaped to releasably retain the O-ball 34' in snap-fit fashion. An outer section 56 of the recess 52 is shaped to rotatably engage the nut when the O-ball 34' is fully received into the inner chamber 54.

Figures 8, 9, 10:
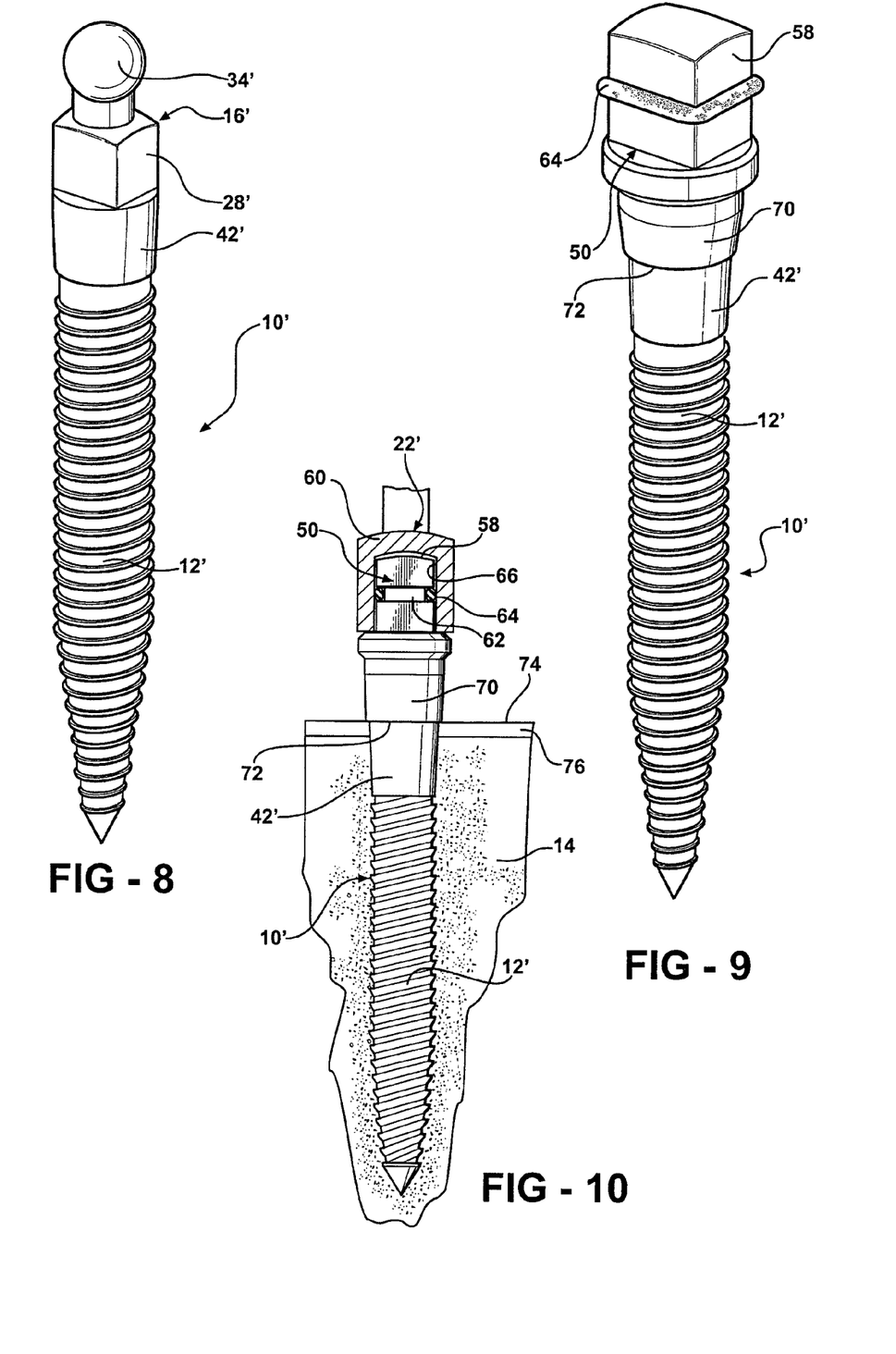
FIG. 8 is a front isometric view of a prosthetic mounting device constructed according to a second embodiment of the invention.
FIG. 9 is an isometric view of a driver adapter supported on the mounting device of FIG. 8.
FIG. 10 is a front view of a ratchet wrench engaging the driver adapter of FIG. 9 and showing a threaded portion of the mounting device disposed in bone tissue.
Figure 11:
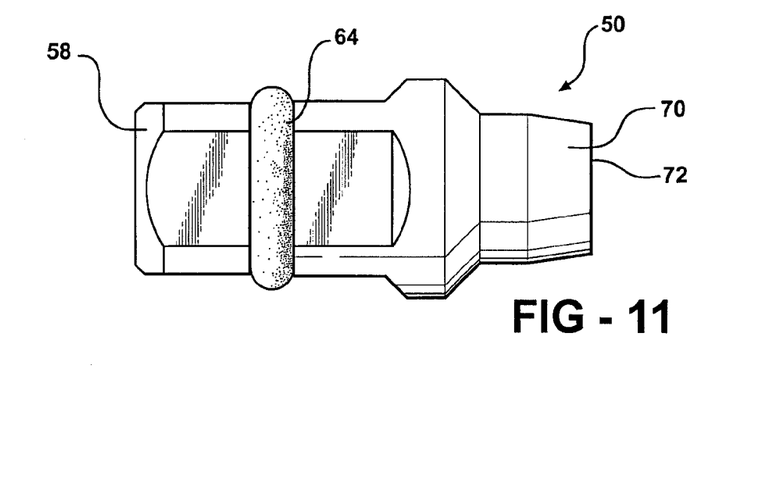
FIG. 11 is a front view of the driver adapter of FIG. 9.
Figure 12:
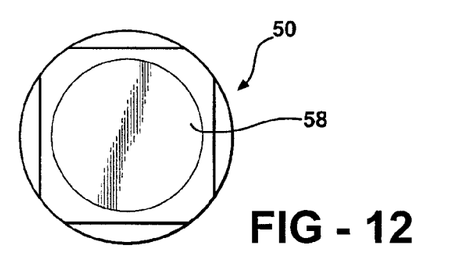
FIG. 12 is an end view of the driver adapter of FIG. 11.
Figure 15:
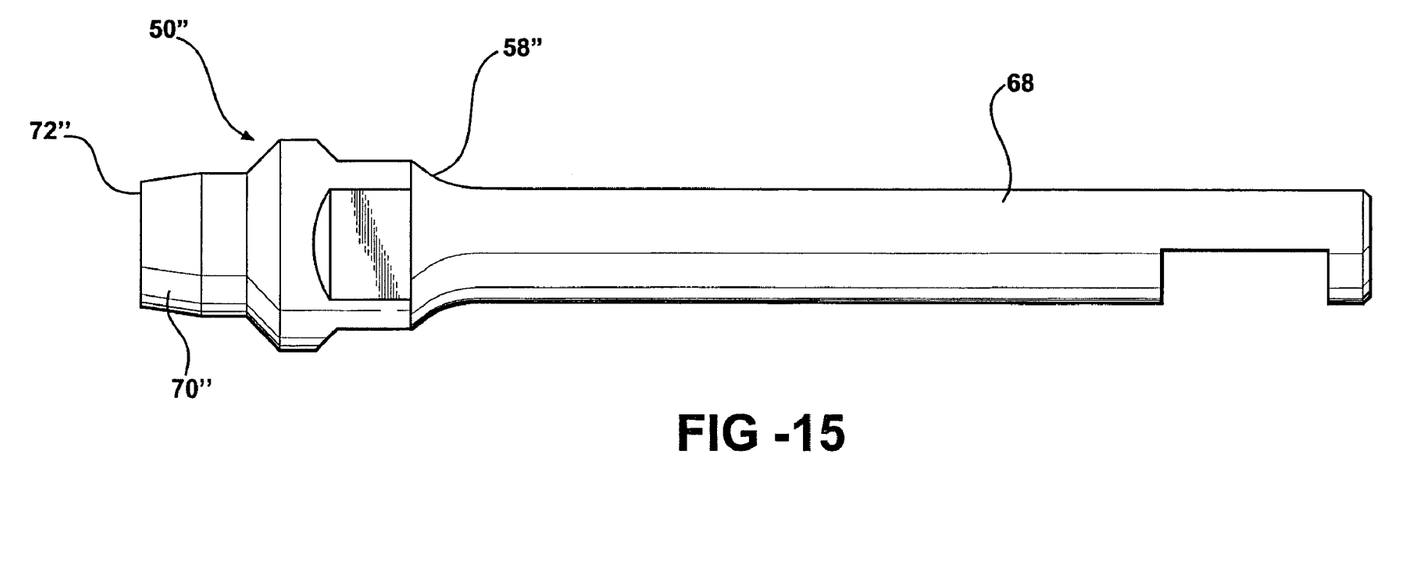
FIG. 15 is a front view of an alternative driver adapter embodiment.

An upper end 58 of the driver adapter 50 has a generally square cross-section shaped to be received into and rotatably engaged by a socket portion 60 a standard ratchet wrench 22' as shown in FIG. 10. A peripheral trench 62 is formed around the upper end 58 of the driver adapter 50 and a rubber O-ring 64 is received into the trench 62 as shown in FIGS. 9, 10, 12, and 13. The O-ring 64 provides an interference fit between the upper end 58 of the driver adapter 50 and an inner surface 66 of a ratchet wrench 22' that prevents the driver adapter 50 from falling out of a ratchet wrench 22' during transport to an osteotomy site. In other embodiments, such as the one shown in FIG. 15, a contra-angle drill adapter shaft 68 may be attached to or integrally formed with the driver adapter 50" and extend axially from the upper end 58" of the driver adapter 50". Such a contra-angle shaft would allow an installer to use a contra-angle drill to install the device. In either case, an installer can engage the mounting device 10', using either a ratchet wrench 22' or a contra-angle drill, and remove the device 10' from its sterile packaging without contaminating the device. The installer can then transport the mounting device 10' to an osteotomy site and install the device without ever touching or otherwise contaminating it.

The driver adapter recess 52 is defined by a socket 70 having a leading rim 72 positioned to contact an upper surface 74 of a gingival tissue layer 76 when the threaded shaft portion 12' of the prosthetic mounting device 10' has been driven to a proper depth into bone tissue 78 beneath the gingival tissue layer 76, i.e., a depth at which the abutment 16' is supported in a position such that a prosthetic mounted on the abutment 16' will generally abut the upper surface 74 of the gingival tissue layer 76 as shown in FIG. 10.

The leading rim 72 of the driver adapter socket 70 is also positioned to contact the upper surface 74 of the gingival tissue layer 76 when the threaded shaft portion 12' of the prosthetic mounting device 10' has been driven to a depth into bone 78 that leaves an upper portion of the collar 42' protruding from an upper surface 80 of the bone 78. In this position, and as best shown in FIG. 10, the protruding upper portion of the collar 42' laterally abuts a surrounding portion of a gingival tissue layer overlying the bone.

To accurately secure a prosthetic device in bone tissue to a proper or desired depth, the driver adapter 50 is connected to the mounting device 10' such that the axially inner chamber 54 of the recess 52 engages and axially retains the O-ball 34' and an axially outer portion 56 of the recess 52 rotatably engages the nut 28'. A rotary driver 22' is then connected to the driver adapter 50. The mounting device 10' is then screwed into bone tissue 78 by engaging the threaded shaft 12' in the bone tissue 78 and operating the rotary driver 22' to rotate the driver adapter 50 and mounting device 10'. Proper mounting device depth is determined as being the depth of the mounting device 10' when the leading rim 72 of the driver adapter socket 70 contacts the upper surface 74 of the gingival tissue layer 76 as shown in FIG. 10.

This description is intended to illustrate certain embodiments of the invention rather than to limit the invention. Therefore, it uses descriptive rather than limiting words. Obviously, it's possible to modify this invention from what the description teaches. Within the scope of the claims, one may practice the invention other than as described.

What is claimed is:

1. A prosthetic mounting device for securing a prosthetic device on bone tissue, the device comprising:
   a threaded shaft configured to be screwed into bone tissue;
   a prosthetic abutment attached to and axially extending from an aft end of the shaft, the abutment being configured to engage and rigidly support a prosthesis, the abutment including an O-ball and a nut disposed between the O-ball and the threaded shaft; and
   a collar extending radially outward from around the aft end of the threaded shaft and shaped for threaded insertion of the device to a depth that leaves protruding from bone an upper portion of the collar of sufficient height to laterally abut surrounding gingival tissue while supporting a prosthetic at a proper height; the shaft, abutment, and collar being formed together as a single unitary piece, the collar including a frustoconical surface tapering radially outward from the threaded portion of the shaft to a plane generally transverse to a longitudinal axis of the shaft and adjacent the aft end of the shaft.

2. A prosthetic mounting device as defined in claim 1 in which the threaded shaft is tapered at a forward end opposite the aft end.

3. A prosthetic mounting device as defined in claim 1 in which the device comprises a titanium alloy.

4. A prosthetic mounting device as defined in claim 1 in which the nut is fixed to and axially extends from the aft end of the threaded shaft and is configured to be engaged and rotated by a tool adapted for that purpose.

5. A prosthetic mounting device as defined in claim 4 in which the nut has a square cross section as measured perpendicular to a rotational axis of the device.

6. A prosthetic mounting device as defined in claim 4 in which the O-ball fixed to and axially extending from an aft end of the nut is configured to engage an O-ring disposed within a prosthesis to be mounted on the device.

7. A prosthetic mounting device as defined in claim 1 in which the threaded shaft is configured to self-tap into a small pilot hole formed in bone tissue.

8. A method for securing a prosthetic device on bone tissue by:
  providing a prosthetic mounting device comprising a prosthetic abutment attached to and axially extending from an aft end of a threaded shaft, the abutment including an O-ball and a nut disposed between the O-ball and the threaded shaft;
  providing a driver adapter comprising a recess configured to receive the O-ball and nut, to releasably retain the O-ball, and to drivingly and releasably engage the nut;
  connecting the driver adapter to the mounting device such that an inner chamber of the recess engages and axially retains the O-ball and an outer portion of the recess rotatably engages the nut;
  connecting a rotary driver to the driver adapter; and
  screwing the mounting device into bone tissue by engaging the threaded shaft with the bone tissue and operating the rotary driver to rotate the driver adapter and mounting device.

9. A prosthetic mounting system for securing a prosthetic device on bone tissue, the system comprising:
  a prosthetic mounting device including a prosthetic abutment attached to and axially extending from an aft end of a threaded shaft, the abutment including a nut;
  a collar that extends radially outward from around the aft end of the threaded shaft; and
  a driver adapter having a recess configured to receive and to releasably and drivingly engage the nut, the driver adapter recess being defined by a socket having a leading rim positioned to contact an upper surface of a gingival tissue layer when the threaded shaft portion of the prosthetic mounting device has been driven to a depth into bone that leaves protruding from an upper surface of the bone an upper portion of the collar, the protruding upper portion of the collar laterally abutting a surrounding portion of a gingival tissue layer overlying the bone.

10. A prosthetic mounting system as set forth in claim 9 in which:
  the prosthetic mounting device abutment includes an O-ball;
  the nut of the abutment is disposed between the O-ball and the threaded shaft; and
  the driver adapter recess is configured to receive and releasably retain the O-ball.

11. A method for securing a prosthetic device on bone tissue by:
  providing a prosthetic mounting device comprising a prosthetic abutment attached to and axially extending from an aft end of a threaded shaft, the abutment including a nut disposed adjacent the threaded shaft;
  providing a driver adapter comprising a recess configured to drivingly and releasably engage the nut at a depth within the recess that places the mounting device at a desired depth when a leading rim of the driver adapter contacts gingival tissue;
  connecting the driver adapter to the mounting device such that an axially outer portion of the recess rotatably engages the nut;
  connecting a rotary driver to the driver adapter;
  screwing the mounting device into bone tissue by engaging the threaded shaft in the bone tissue and operating the rotary driver to rotate the driver adapter and mounting device;
  determining proper mounting device depth as being the depth of the mounting device when the leading rim of the driver adapter socket contacts gingival tissue.

12. The method of claim 11 in which:
  the step of providing a prosthetic mounting device includes providing such a device that includes an abutment having an O-ball, and the nut is disposed between the O-ball and the threaded shaft;
  the step of providing a driver adapter includes providing such an adapter that includes a recess configured to receive the O-ball and nut and to releasably retain the O-ball; and
  the step of connecting the driver adapter to the mounting device includes connecting the driver adapter to the mounting device such that an axially inner chamber of the recess engages and axially retains the O-ball.

13. The method of claim 11 in which:
  a small pilot hole is formed in bone tissue at a desired location for mounting device insertion before the step of screwing the mounting device into bone tissue; and
  the step of screwing the mounting device into bone tissue includes the additional step of engaging the threaded shaft in the pilot hole.

* * * * *

UNITED STATES PATENT AND TRADEMARK OFFICE
CERTIFICATE OF CORRECTION

PATENT NO. : 7,033,174 B2  Page 1 of 1
APPLICATION NO. : 10/165332
DATED : April 25, 2006
INVENTOR(S) : Thierry Giomo It is certified that error appears in the above-identified patent and that said Letters Patent is hereby corrected as shown below:

Column 2, line 33, after "allows it" insert --to--
Column 3, line 10, after "is encountered" insert --and--
Column 4, line 37, after "In this" delete "positino" and insert --position--
Column 5, line 39, after "embodiment" delete ";" and insert --.--
Column 6, line 53, delete the "12" after "portion"
Column 7, line 1, delete the second "14" (the "14" that comes before "covering")
Column 7, line 26, after "can" delete "comprise" and insert --compromise--

Signed and Sealed this

Nineteenth Day of September, 2006

JON W. DUDAS
*Director of the United States Patent and Trademark Office*